United States Patent [19]

Racz et al.

[11] 4,295,465
[45] Oct. 20, 1981

[54] LARYNGOSCOPE BLADE

[75] Inventors: Gabor Racz, Lubbock, Tex.; Forrest Allen, Fayetteville, N.Y.

[73] Assignee: N.A.D., Inc., Telford, Pa.

[21] Appl. No.: 137,057

[22] Filed: Apr. 3, 1980

[51] Int. Cl.³ .............................................. A61B 1/06
[52] U.S. Cl. ...................................... 128/11; 128/16; 128/18
[58] Field of Search .................. 128/11, 3, 10, 15, 16, 128/17, 18, 20

[56] References Cited

U.S. PATENT DOCUMENTS

| | | | |
|---|---|---|---|
| 1,510,304 | 9/1924 | Cameron | 128/16 |
| 1,908,010 | 5/1933 | Cameron | 128/16 |
| 2,070,820 | 2/1937 | Allyn | 128/11 |
| 2,289,226 | 7/1942 | von Foregger | 128/11 |
| 2,648,329 | 8/1953 | Morch | 128/11 |
| 3,363,622 | 1/1968 | Mendola | 128/15 |
| 3,507,272 | 4/1970 | Laerdal | 128/16 |
| 3,638,644 | 2/1972 | Reick | 128/16 |
| 3,771,514 | 11/1973 | Huffman et al. | 128/11 |
| 3,826,248 | 7/1974 | Gobels | 128/11 |
| 3,856,001 | 12/1974 | Phillips | 128/11 |
| 3,884,222 | 5/1975 | Moore | 128/11 |
| 3,943,920 | 3/1976 | Kandel | 128/11 |
| 3,986,854 | 10/1976 | Scrivo et al. | 128/16 X |
| 4,112,933 | 9/1978 | Moses | 128/11 |
| 4,114,609 | 9/1977 | Moses | 128/11 |
| 4,126,127 | 11/1978 | May | 128/11 |

OTHER PUBLICATIONS

Air Products & Chemicals, Inc., Anesthesia Equipment Catalog, 1976.

Primary Examiner—Robert W. Michell
Assistant Examiner—Nancy A. B. Swisher
Attorney, Agent, or Firm—Caesar, Rivise, Bernstein & Cohen, Ltd.

[57] ABSTRACT

A blade for a layrngoscope. The blade comprises a base portion and a projecting flange portion. The flange portion extends along part of the base portion and is pivotably mounted with respect thereto. Biasing means provide a preselected bias force on the flange portion to hold the flange portion in its projecting position. If in using the blade the flange portion contacts the patient's teeth, the flange pivots when the force applied to the teeth exceeds the predetermined bias force.

10 Claims, 3 Drawing Figures

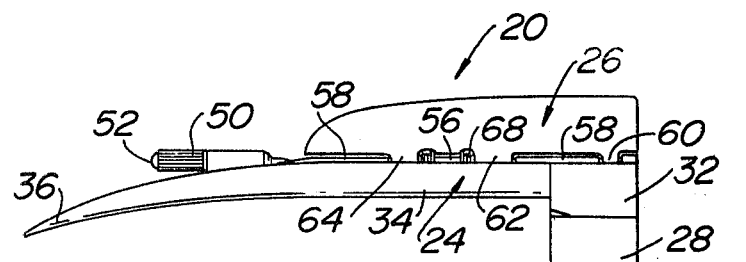
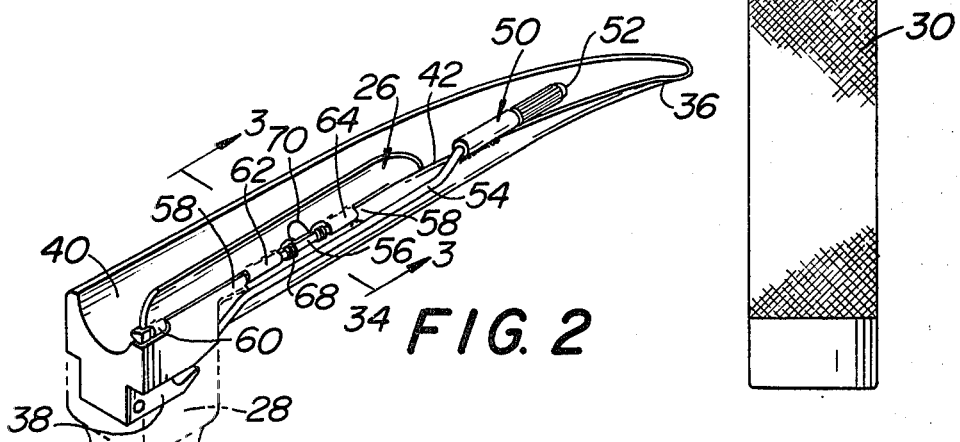
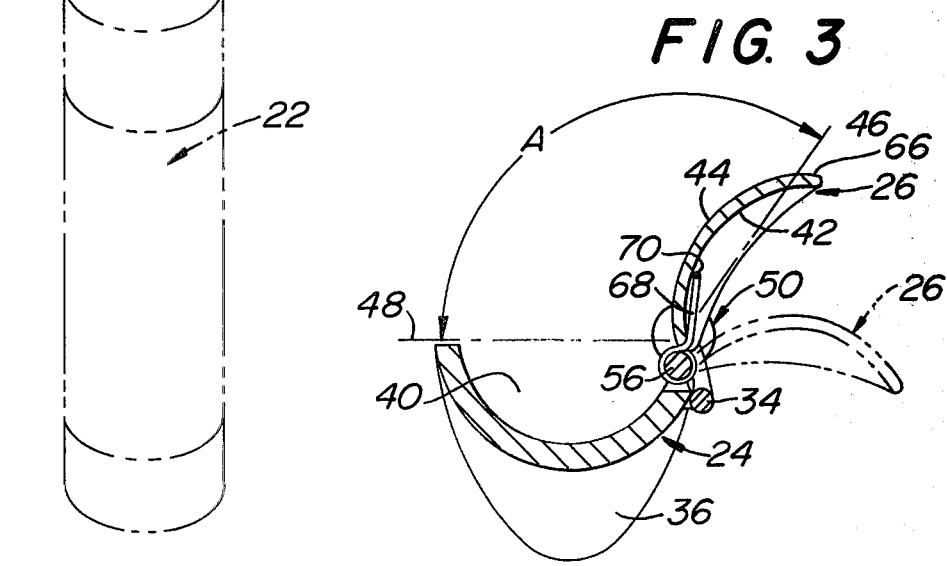

LARYNGOSCOPE BLADE

This invention relates generally to laryngoscopes and more particularly to blades therefor.

Laryngoscopes generally employed in medicine basically comprise a handle from which a blade or spatula projects. The blade serves as a means for facilitating the inspection of the larynx or the insertion of anesthetic breathing tubes and commonly includes a projecting flange which extends along the blade a substantial distance towards the tip of the blade. Frequently, illuminating means are provided for lighting the throat when the laryngoscope is used. To that end, light bulbs, lamps, or fiberoptics are generally provided mounted along the blade and under the flange and are energized by batteries housed in the handle.

While there are numerous types of laryngoscope blades commercially available, such blades generally fall into two categories, namely, curved blades and straight blades. The curved blades are used to expose the larynx by putting the tip of the blade in front of the epiglottis, lifting up and away on the laryngoscope handle, thereby resulting in displacement action of the epiglottis by pulling on the hyoepiglottic ligament. This allows the direct visualization of the vocal chords to enable the placement of an endotracheal tube while directly examining the chords. Straight blades are used in a slightly different manner. To that end, the tip of the straight blade laryngoscope may be placed behind the epiglottis for lifting the epiglottis directly from its covering position to visualize the vocal chords. Straight blades having a curvature at the tip are available and can be used by placing the tip in front of the epiglottis to lift the epiglottis away by pulling on the hyoepiglottic ligament or by direct displacement of the epiglottis forward when the blade is placed behind the epiglottis.

Prior art laryngoscsope blades, irrespective of their shape, exhibit a tendency to damage the patient's teeth during endoscopy for endotracheal intubation. Such damage results from the application of excess pressure to the teeth, primarily the upper incisors, by the flange making contact therewith when the blade is used to visualize the larynx.

While it has been recognized that conventional laryngoscope blades do pose a potential hazard to teeth, very few attempts have been made to modify such blades to obviate the hazard. Instead, the precautionary technique of folding a bandage or other pressure absorbing material between the teeth and the blade to prevent excess pressure thereon is frequently adopted. However, such a technique is time consuming, is not uniformly effective and depends upon the skill of the administering personnel.

It has been suggested to form a laryngoscope blade of a soft plastic material so that the application of pressure on the teeth during use will not result in damage thereto. In this regard, in U.S. Pat. No. 3,507,272 (Laerdal) there is disclosed a laryngoscope having a spatula formed of a soft plastic.

While the use of a soft plastic for a laryngoscope blade may be an effective means to obviate the danger of tooth injury, such a solution is not without its own disadvantages, e.g., difficulty in sterilizing, resistance to deformation, limited reuse, etc.

Accordingly, it is a general object of the instant invention to provide a laryngoscope blade which overcomes the disadvantages of the prior art.

It is a further object of the instant invention to provide a laryngoscope blade which can be formed of conventional materials, such as metal, and which when used will not pose a hazard to the patient's teeth.

It is still a further object of the instant invention to provide a laryngoscope blade including means to enable the deformation of a portion thereof in the event that excess force is attempted to be applied to the patient's teeth.

These and other objects of the instant invention are achieved by providing a laryngoscope blade for a laryngoscope comprising a base member and a projecting flange member. The base member is an elongated member comprising a rear portion, a mid-portion, and a tip portion. The rear portion is arranged for securement to a laryngoscope handle. The mid-portion is generally linear. The flange projects upward from the base member along the rear and mid-portions and is pivotly connected by resilient means to the base member so that when the blade is inserted into a patient's mouth with the tip portion disposed adjacent the epiglottis, the flange is enabled to pivot with respect to the blade to prevent the application of excess pressure on the patient's teeth.

Other objects and many of the attendant advantages of this invention will be readily appreciated as the same becomes better understood by reference to the following detailed description when considered in connection with the accompanying drawings wherein:

FIG. 1 is a side elevational view of the laryngoscope blade in accordance with the instant invention mounted on a conventional laryngoscope handle;

FIG. 2 is an enlarged perspective view of the laryngoscope blade shown in FIG. 1 and with the handle shown by phantom lines; and FIG. 3 is an enlarged sectional view taken along line 3—3 of FIG. 2.

Referring now to the various figures of the drawing wherein like reference characters refer to like parts, there is shown generally at 20 in FIG. 1 a laryngoscope blade constructed in accordance with the instant invention shown mounted on a laryngoscope handle 22. The blade 20 basically comprises an elongated base member 24 and a projecting flange 26. The handle 22 is of conventional construction and includes an upper end including a connector 28. The blade 20 is arranged for releasable securement to the handle, via connector 28. As is conventional the handle 22 is hollow for receipt of a battery or other electrical power supply means to effect the illumination of the tip of the blade 20 by illuminating means (to be described later). The outer surface 30 of the handle is knurled to provide a good manual gripping surface.

It must be pointed out at this juncture that while the blade 20 shown in FIG. 1 is shown arranged for releasable securement to the handle 22, the blade 20 may be formed integrally with the handle or permanently secured thereto, as desired, to form a complete laryngoscope.

The blade portion 24 includes a rear portion 32, a midportion 34 and a tip portion 36. The rear portion 32 includes connecting means 38 of conventional construction and arranged for engagement and releasable securement to the connector 28 of handle 22. As can be clearly seen in FIGS. 1 and 2, the midportion of the blade is substantially linear and terminates in the free front end or tip 36. The tip 36 curves slightly downward from the linear portion 34. As shown clearly in FIGS. 2 and 3, the blade member 24 is generally trough or concave shaped in cross-section along its entire length, i.e., it includes a concave recess 40 along its entire length. The flange 26 is secured to one side of the blade member 24 at the peripheral edge 42.

The flange 26 is an elongated trough or concave (C-shaped) member which is substantially linear in the longitudinal direction and extends along the blade from the rear portion 32 to the point at which the mid-portion 34 merges with the tip portion 36. The transverse axis of the flange is denoted generally by the reference numeral 46. The blade portion 24 is also generally C-shaped along its length and includes a transverse axis, denoted by the reference numeral 48.

As shown in FIG. 3, the flange 26 is mounted on the blade portion 24 so that its transverse axis 46 lies at an angle A which is greater than 90° to the transverse axis 48 of the blade portion 24. This feature insures proper operation of the blade as will be described in detail later.

In order to effect the illumination of the tip 36 of the blade when the blade is in use, conventional illuminating means 50 are mounted on the blade. The means 50 comprises a lamp 52 mounted within a cylindrical housing on the edge 42 of the blade immediately adjacent the tip 36. An electrical conductor 54 extends along the side of the blade portion 34 and terminates at an electrical connector (not shown) at the rear portion 32 of the blade. The connector electrically connects the lamp to a battery (not shown) disposed within the handle 22 when the blade is secured to the handle.

As mentioned heretofore, the flange 26 is mounted on the blade so that it can pivot with respect thereto. This feature is of utmost importance to insure that the flange does not damage the patient's teeth when the laryngoscope is used. Accordingly, the flange 26 is mounted on the blade 24, via pivoting means 56. The pivoting means 56 basically comprises a pivot shaft or pin 58 extending along edge 42 of the blade member 24. The pin 58 is journaled in longitudinal aligned passageways 58 in the edge 42 of the blade. The flange 26 includes three longitudinally aligned passageways, 60, 62 and 64 in the lower edge thereof. The passageways are arranged to receive the pivot pin 58. When the pivot pin is located within the aligned passageways 60, 62 and 64 in the flange and the aligned passageways 58 in the blade portion 24, the blade can pivot clockwise about the longitudinal axis of the pin from the generally upwardly projecting position shown by full lines in FIG. 3 to the phantom line position shown therein.

The flange is normally biased in the generally upwardly projecting position shown in FIG. 3 by resilient means 66. To that end the resilient means applies a predetermined bias force on the flange to hold it in said position. The flange is permitted to pivot about pin 56 in the clockwise direction of FIG. 3 toward the phantom line position when the force applied to the upper surface of the flange exceeds the predetermined bias force provided by the resilient means. In accordance with a preferred aspect of this invention the predetermined force applied by the bias means 66 is selected to be within the normal bite pressure range experienced by persons during chewing. Accordingly, when the blade of the instant invention is used, if the force applied to the tooth by the upper surface, i.e., portion 66 of the flange, exceeds the predetermined bias force, the flange pivots in the clockwise direction as shown in FIG. 3 toward the phantom line position. As will be appreciated by those skilled in the art the amount of deflection of the flange is a function of the amount of force or pressure applied by the laryngoscope in excess of the bias force.

While various resilient means can be used to bias the flange in the preferred embodiment shown herein, the resilient means comprises a helical spring 68. The spring includes a pair of helical ends 69 wrapped around the pivot pin 56 and a mid-loop portion 70 engaging the inner surface 42 of the flange 26. The midloop portion 70 applies a bias force to the flange in the counter clockwise direction as viewed in FIG. 3.

As noted heretofore, the flange 26 is arranged to be normally positioned so that its transverse axis 46 is at an angle "A" which is greater than 90° to the transverse axis 48 of the blade portion 24. This feature is of considerable importance in that it insures that when the flange portion 66 contacts the patient's teeth, the moment of force applied to the flange is offset or beyond the longitudinal axis of the pivot pin so that the flange automatically pivots in the clockwise direction as shown in FIG. 3. Such action precludes counter-clockwise rotation which could impede the visualization of the larynx or could interfere with any tube lying along the trough shaped surface 40 of the blade portion 24.

The blade of the instant invention can be formed of any suitable material, e.g., stainless steel, chrome-plated brass, plastic, etc., so long as the flange portion is pivotably mounted on the blade portion by resilient means which applies a bias force thereto. While the resilient means is shown as comprising a spring, other resilient biasing means can be utilized. For example, the flange and the blade portion 24 may be formed integrally with one another and having a living hinge therebetween.

Inasmuch as the stresses normally applied to the teeth during mastication vary from approximately 25 pounds to 275 pounds, with the average force being approximately 170 pounds, in order to avoid excessive pressure to the upper teeth during use of the blade, the resilient means can be arranged to apply a biasing force at approximately 10 to 15 pounds on the flange.

The blades of this invention are constructed in various sizes to accommodate various types of patients. For example, a No. 2 adult blade of this invention is approximately 6.0 inches (15.24 cm) long, while a No. 3 adult blade is approximately 7.0 inches (17.78 cm) long.

As will be appreciated from the foregoing, the blade of the instant invention is simple in construction, is compatible with existing blades and can be used in a similar manner as existing blades, yet does not pose a significant hazard to teeth during use. Moreover, in the event that the endoscopist must apply greater pressure to the teeth to accomplish the desired medical procedure, the deflection of the flange portion of the blade will least alert the endoscopist to the possibility of injury to the teeth.

Without further elaboration, the foregoing will so fully illustrate our invention that others may, by applying current or future knowledge, readily adapt the same for use under various conditions of service.

What is claimed as the invention is:

1. A blade for a laryngoscope having a handle, said blade comprising a base member and a projecting flange member, and bias means, said base member being an elongated member having a rear portion, a midportion and a tip portion, said blade being secured to said handle at said rear portion said midportion being generally linear, said flange projecting upward from said base member along said rear and midportion and being pivotly mounted on said base member, said bias means providing a bias force to said blade, whereupon when said blade is inserted into a patient's mouth with flange in contact with the patient's teeth, said flange is enabled to pivot with respect to said blade against the force provided by said bias means to prevent the application of excess pressure to the teeth.

2. The blade of claim 1 wherein said blade is generally trough shaped along its length and wherein said flange is generally trough shaped along its length.

3. The blade of claim 2 wherein said tip portion is curved.

4. The blade of claim 3 wherein said bias means comprises a resilient spring.

5. The blade of claim 3 wherein said blade includes illuminating means.

6. The blade of claim 1 wherein said flange includes a tooth engaging surface disposed at an angle slightly greater than 90° to the mid-portion of the blade.

7. The blade of claim 6 wherein said blade is generally trough shaped along its length and wherein said flange is generally trough shaped along its length.

8. The blade of claim 7 wherein said tip portion is curved.

9. The blade of claim 8 wherein said bias means comprises a resilient spring.

10. The blade of claim 9 wherein said blade includes illuminating means.

* * * * *